(12) United States Patent
Kapadia et al.

(10) Patent No.: US 12,186,134 B2
(45) Date of Patent: Jan. 7, 2025

(54) INSTRUMENT DRIVE UNIT TORQUE COMPENSATION USING INERTIAL MEASUREMENT UNIT

(71) Applicant: Covidien LP, Mansfield, MA (US)

(72) Inventors: Jaimeen V. Kapadia, Cambridge, MA (US); Richard S. Lech, Hamden, CT (US)

(73) Assignee: Covidien LP, Mansfield, MA (US)

( * ) Notice: Subject to any disclaimer, the term of this patent is extended or adjusted under 35 U.S.C. 154(b) by 623 days.

(21) Appl. No.: 17/431,473

(22) PCT Filed: Mar. 10, 2020

(86) PCT No.: PCT/US2020/021917
§ 371 (c)(1),
(2) Date: Aug. 17, 2021

(87) PCT Pub. No.: WO2020/185797
PCT Pub. Date: Sep. 17, 2020

(65) Prior Publication Data
US 2022/0125545 A1 Apr. 28, 2022

Related U.S. Application Data

(60) Provisional application No. 62/818,250, filed on Mar. 14, 2019.

(51) Int. Cl.
*A61B 34/30* (2016.01)
*A61B 90/00* (2016.01)
(Continued)

(52) U.S. Cl.
CPC ............. *A61B 90/03* (2016.02); *A61B 34/30* (2016.02); *B25J 9/1638* (2013.01);
(Continued)

(58) Field of Classification Search
CPC . A61B 90/03; A61B 34/30; A61B 2034/2048; A61B 2090/031;
(Continued)

(56) References Cited

U.S. PATENT DOCUMENTS 8,828,023 B2  9/2014  Neff et al.
2010/0094312 A1  4/2010  Ruiz Morales et al.
(Continued)

FOREIGN PATENT DOCUMENTS

EP       1915963 A1      4/2008
WO    2014022786 A2      2/2014
(Continued)

OTHER PUBLICATIONS

Chinese Office Action dated Aug. 24, 2023 for Chinese Patent Application No. 202080018171.0 (12 pages).
(Continued)

*Primary Examiner* — George Manuel
(74) *Attorney, Agent, or Firm* — Carter, DeLuca & Farrell LLP (57) ABSTRACT

An instrument drive unit includes a housing defining a central longitudinal axis; an inertial measurement unit disposed within the housing and configured to determine a pose of the instrument drive unit; and a controller disposed within the housing, the controller configured to receive the pose of the instrument drive unit from the inertial measurement unit and to generate a corrected output signal which compensates for the pose of the instrument drive unit.

15 Claims, 10 Drawing Sheets

(51) Int. Cl.
*B25J 9/16* (2006.01)
*A61B 34/20* (2016.01)
*A61B 34/37* (2016.01)

(52) U.S. Cl.
CPC ....... *A61B 2034/2048* (2016.02); *A61B 34/37* (2016.02); *A61B 2090/031* (2016.02); *A61B 2090/066* (2016.02); *G05B 2219/39178* (2013.01); *G05B 2219/39194* (2013.01); *G05B 2219/45117* (2013.01)

(58) Field of Classification Search
CPC .... A61B 2090/066; A61B 2017/00017; A61B 2090/371; A61B 2090/373; A61B 2090/376; A61B 2090/378; A61B 34/37; B25J 9/1638; G05B 2219/39178; G05B 2219/39194; G05B 2219/45117
See application file for complete search history.

(56) References Cited

U.S. PATENT DOCUMENTS

| | | | |
|---|---|---|---|
| 2014/0052154 A1 | 2/2014 | Griffiths et al. | |
| 2014/0303643 A1 | 10/2014 | Ha et al. | |
| 2015/0066051 A1 | 3/2015 | Kwon et al. | |
| 2018/0153634 A1* | 6/2018 | Zemlok | A61B 34/71 |
| 2018/0280098 A1 | 10/2018 | Griffiths et al. | |
| 2019/0143506 A1* | 5/2019 | Rabindran | B25J 3/04 700/253 |
| 2019/0175286 A1* | 6/2019 | Zhou | A61B 34/70 |
| 2020/0261169 A1* | 8/2020 | Miller | B25J 9/1607 |
| 2021/0212777 A1 | 7/2021 | Cheng | |
| 2021/0401519 A1* | 12/2021 | Gomez | A61B 90/06 |

FOREIGN PATENT DOCUMENTS

| | | | |
|---|---|---|---|
| WO | 2017040821 A1 | 3/2017 | |
| WO | 2017147596 A1 | 8/2017 | |
| WO | WO2017171996 * | 9/2017 | A61B 34/30 |
| WO | 2018075784 A1 | 4/2018 | |
| WO | 2020118149 A1 | 6/2020 | |
| WO | 2020163263 A1 | 8/2020 | |

OTHER PUBLICATIONS

International Search Report mailed Jun. 30, 2020 and Written Opinion completed Jun. 30, 2020 corresponding to counterpart Int'l Patent Application PCT/US20/21917.
Extended European Search Report dated Nov. 21, 2022 corresponding to counterpart Patent Application EP 20770885.0.
Chinese First Office Action dated Mar. 10, 2023 corresponding to counterpart Patent Application CN 202080018171.0.
Office Action issued in corresponding Chinese Application No. 2020800181710 mailed Apr. 30, 2024, together with English language translation (11 pages).

* cited by examiner

INSTRUMENT DRIVE UNIT TORQUE COMPENSATION USING INERTIAL MEASUREMENT UNIT

CROSS-REFERENCE TO RELATED APPLICATIONS

The present application is a U.S. National Stage Application filed under 35 U.S.C. § 371 (a) claiming the benefit of and priority to International Patent Application No. PCT/US20/21917, filed Mar. 10, 2020, which claims the benefit of and priority to U.S. Provisional Patent Application Ser. No. 62/818,250, filed Mar. 14, 2019, the entire disclosures of each of which being incorporated by reference herein.

FIELD OF THE INVENTION

The present invention relates to robotic surgical systems used in minimally invasive medical procedures because of their increased accuracy and expediency relative to handheld surgical instruments.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector of a surgical instrument that acts on a patient. The user interface includes an input controller or handle that is moveable by the surgeon to control the robotic surgical system and a display allowing the surgeon to visualize the surgical instrument within a surgical site.

The surgical instrument is supported by an arm of a surgical robot. The arm of the surgical robot includes a setup arm and a linkage that are movable within the surgical environment to manipulate the surgical instrument. The linkage is supported by the setup arm and supports the surgical instrument within the surgical environment. The setup arm may move during the surgical procedure to reposition the linkage and/or to avoid collisions with other arms of the surgical robot.

The linkage supports an instrument drive unit (IDU) that is configured to operate a tool to manipulate tissue. The IDU includes one or more motors that cooperate to operate the tool. As the linkage moves the IDU about a workspace, forces acting on the IDU, and thus the motors within the IDU, vary with the pose of the linkage. For example, the forces of gravity acting on each of the motors may vary with the pose of the linkage.

SUMMARY

There is a need for determining and compensating for the forces acting on the motors of the IDU as the pose of the linkage varies within the workspace.

This disclosure relates generally to an IDU including an inertial measurement unit (IMU) disposed within the IDU to determine forces acting on the motors and a method for compensating for the forces acting on the motors.

In an aspect of the present disclosure, an instrument drive unit is provided and is configured to manipulate a tool. The instrument drive unit includes a housing defining a central longitudinal axis; an inertial measurement unit disposed within the housing and configured to determine a pose of the instrument drive unit; and a controller disposed within the housing, the controller configured to receive the pose of the instrument drive unit from the inertial measurement unit and to generate a corrected output signal which compensates for the pose of the instrument drive unit.

The inertial measurement unit may be disposed about the central longitudinal axis.

The inertial measurement unit may include a gyroscope and an accelerometer.

The inertial measurement unit may be configured to determine the pose of the instrument drive unit based on gravity acting on the inertial measurement unit.

The inertial measurement unit may include a compass.

The instrument drive unit may further include a first motor disposed within the housing. The first motor may be configured to receive the corrected output signal and to manipulate the tool in response to the corrected output signal.

The instrument drive unit may further include a mounting plate at a first end of the instrument drive unit. The first motor may be secured to the mounting plate by a first torque transducer.

The instrument drive unit may further include a rear plate at a second opposite end of the instrument drive unit. The inertial measurement unit may be secured to the rear plate.

The instrument drive unit may still further include a control board extending between the rear plate and the mounting plate. The controller may be disposed on the control board.

The instrument drive unit may further include a first torque sensor disposed within the housing. The first torque sensor may be configured to measure a torque of the first motor.

The instrument drive unit may further include a second motor; a third motor; and a fourth motor. The first, second, third, and fourth motors may be disposed within the housing and arranged about the central longitudinal axis. Each of the second, third, and fourth motors may be configured to receive the corrected output signal and to manipulate the tool in response to the corrected output signal.

The instrument drive unit may still further include a second torque sensor disposed within the housing and configured to measure a torque of the second motor; a third torque sensor disposed within the housing and configured to measure a torque of the third motor; and a fourth torque sensor disposed within the housing and configured to measure a torque of the fourth motor.

According to another aspect of the present disclosure, a surgical robot is provided and includes a base; a linkage supported by the base; and an instrument drive unit supported by the linkage and configured to support and manipulate a tool. The instrument drive unit includes a housing defining a central longitudinal axis; an inertial measurement unit disposed within the housing and configured to determine a pose of the instrument drive unit; and a controller disposed within the housing, the controller configured to receive the pose of the instrument drive unit from the inertial measurement unit and to generate a corrected output signal which compensates for the pose of the instrument drive unit.

The surgical robot may further include a tool supported by the instrument drive unit. The tool may be supported about a tool axis coaxial with the central longitudinal axis.

The inertial measurement unit may be disposed about the central longitudinal axis.

According to still another aspect of the present disclosure, a method of controlling an instrument drive unit with a controller disposed within the instrument drive unit, is provided. The method includes determining a pose of the instrument drive unit by reading values from an inertial measurement unit; calculating a corrected torque based on the pose of the instrument drive unit; and transmitting the corrected torque to a motor of the instrument drive unit.

The method may further include receiving a desired pose of a tool and calculating an output torque to manipulate the tool from the current pose to the desired pose.

The method may further include determining correction values for the IDU based on the pose of the instrument drive unit.

The calculation of the corrected torque may include applying the correction values to the output torque.

The determination of a pose of the instrument drive unit may include measuring gravity acting on the inertial measurement unit with a gyroscope and an accelerometer of the inertial measurement unit.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician or surgical robot manipulating the device or component and the term "distal" refers to the portion of the device or component thereof that is farther from the clinician or surgical robot manipulating the device.

Figure 1:
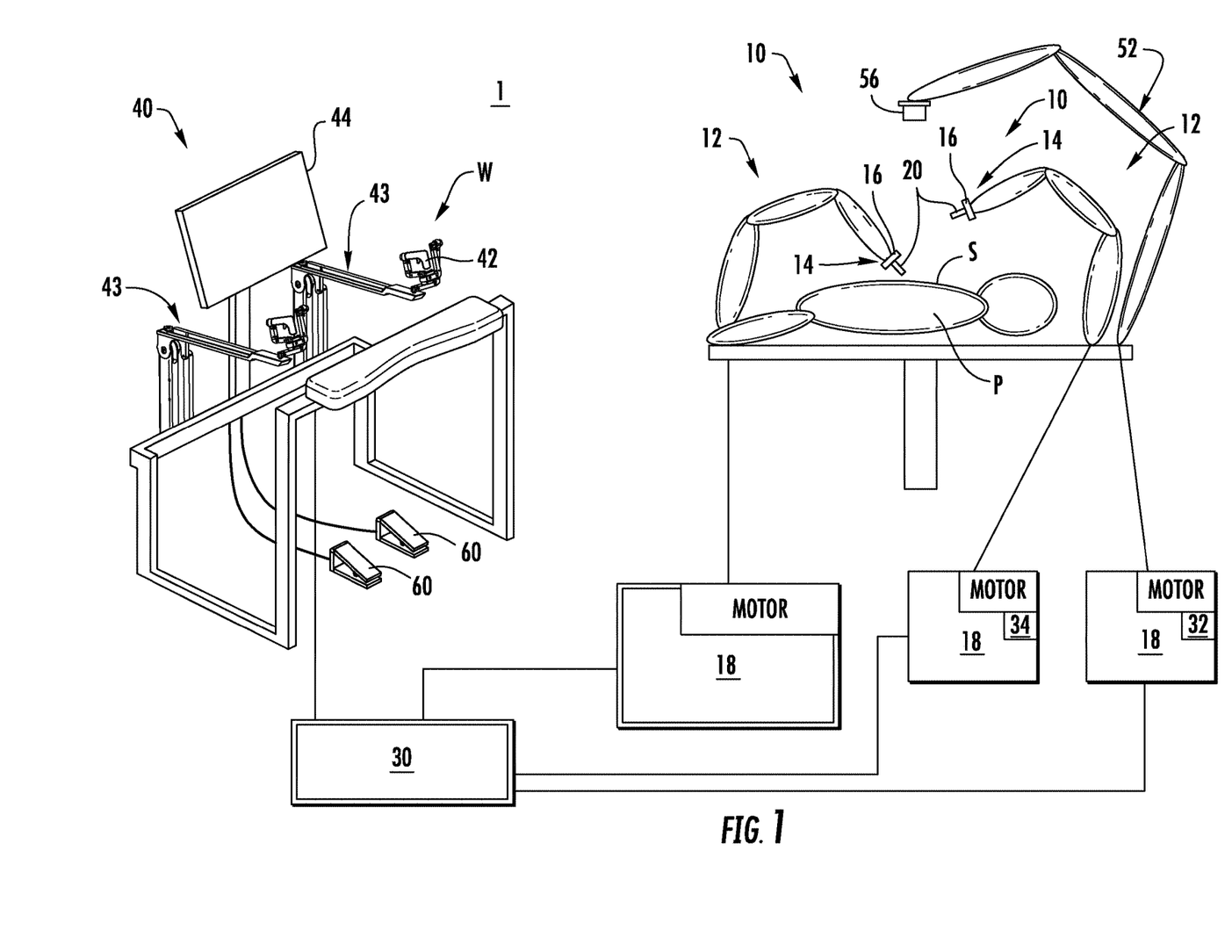
FIG. 1 is a schematic of an exemplary robotic surgical system provided in accordance with the present disclosure.

Referring to FIG. 1, a robotic surgical system 1 in accordance with the present disclosure is shown generally as a surgical robot 10, a processing unit 30, and a user console 40. The surgical robot 10 generally includes linkages or arms 12 and one or more robot bases 18 that each support one of the linkages 12. The linkages 12 moveably support an end effector or tool 20 which is configured to act on tissue. The linkages 12 each have an end 14 that supports the end effector or tool 20 which is configured to act on tissue. In addition, the ends 14 of the linkages 12 may include an imaging device 16 for imaging a surgical site "S". The user console 40 is in communication with the robot bases 18 through the processing unit 30. In addition, the robot bases may each include a controller 32, 34 that is in communication with the processing unit 30.

The user console 40 includes a display device 44 which is configured to display three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user console 40 also includes input handles 42 which are supported on control arms 43 which allow a clinician to manipulate the surgical robot 10 (e.g., move the linkages 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices (not explicitly shown) which allow the surgeon to manipulate (e.g., clamp, grasp, fire, open, close, rotate, thrust, slice, etc.) the tools 20 supported at the ends 14 of the linkages 12.

Each of the input handles 42 is moveable through a predefined workspace to move the ends 14 of the linkages 12, e.g., tools 20, within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to the view captured by the imaging devices 16, 56. In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figure 2:
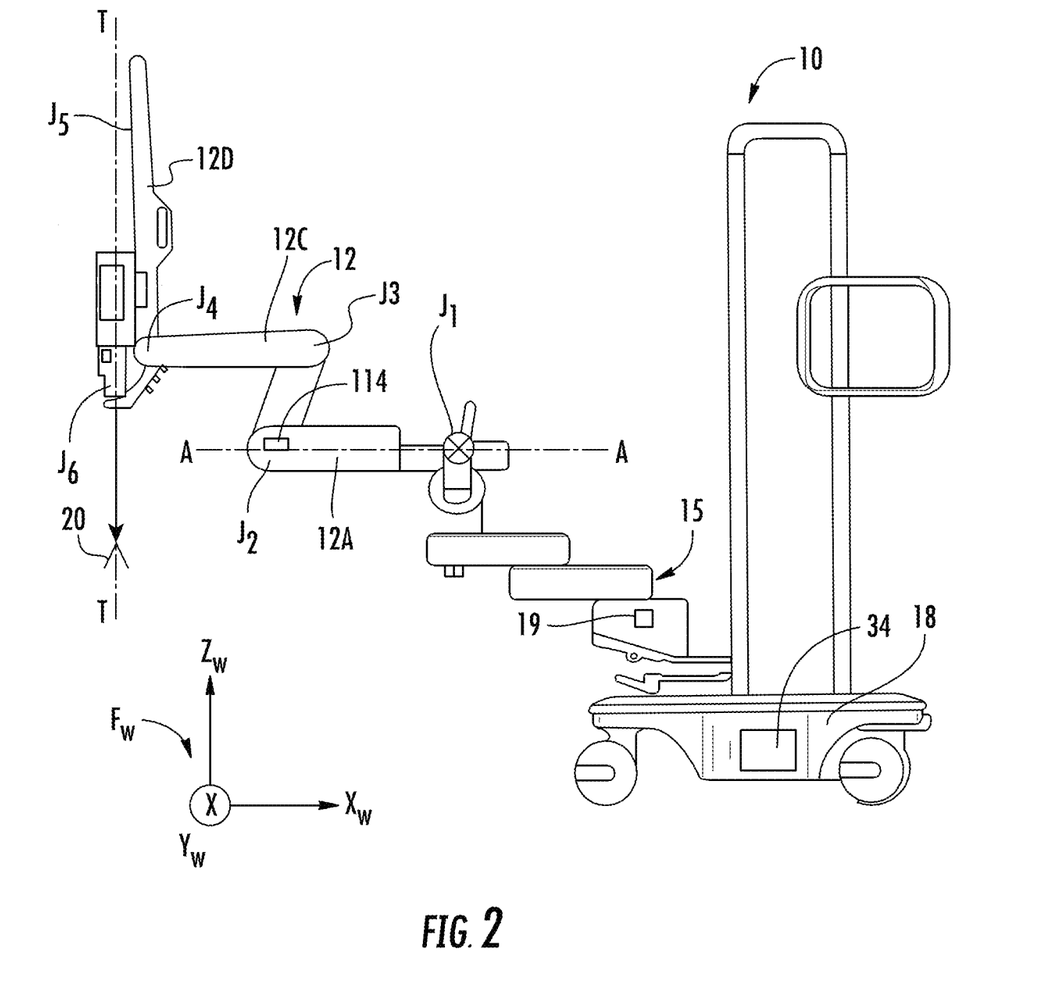
FIG. 2 is a side view of a robot base or cart of a surgical robot of the robotic surgical system of FIG. 1.

Referring to FIG. 2, the surgical robot 10, shown as a robot base or cart 18, has a world frame $F_w$ that is a fixed frame defined by $X_w$-$Y_w$-$Z_w$ axes which remain fixed during a surgical procedure. The world frame $F_w$ is a frame positioned on the floor or ground of a surgical environment that can be referenced by other frames within the surgical environment allowing each frame within the surgical environment a common frame of reference. As shown, the $X_w$ axis is defined in a horizontal direction parallel to the floor, the $Y_w$ axis is defined in a horizontal direction parallel to the floor and orthogonal to the $X_w$ axis, and the $Z_w$ axis is defined in a height direction from the floor to the ceiling and orthogonal to the $X_w$ axis and the $Y_w$ axis. It will be appreciated that the $X_w$ and the $Y_w$ axes define an X-Y plane that is parallel to the floor The robot base 18 includes a setup arm 15 that supports a first portion of a first link 12a of the linkage 12 at a first joint $J_1$ such that a longitudinal axis A-A of the first link 12a is substantially parallel to the X-Y plane defined. The first joint $J_1$ is a single degree of freedom joint which allows the first link 12a to rotate about the first joint about an axis that is substantially orthogonal to the X-Y plane. The first link 12a may be pitched slightly at the first joint $J_1$ such that the longitudinal axis A-A is out of parallel with a horizontal axis that is parallel to the X-Y plane to define a pitch angle. The robot base 18 also includes a brake 19 that has an engaged configuration in which the brake 19 prevents movement of the setup arm 15 and a disengaged or released configuration in which movement of the setup arm 15 is permitted. In some embodiments, the first link 12a may be directly secured to the robot base 18.

As detailed below, the linkage 12 includes a plurality of sensors that can be used to determine the pose of the linkage 12. The pose of the linkage 12 is used as an input for control algorithms that control position and movement of the tool 20. For example, forward or inverse kinematics may be used to control the position of the tool 20 within the world frame $F_w$. In addition, the hand-eye coordination calculations may be used to control the position of the tool 20 within the world frame $F_w$. For a detailed discussion of exemplary kinematic control algorithms, reference can be made to U.S. patent application Ser. No. 16/081,773, filed Aug. 31, 2018, and for a detailed discussion of exemplary hand-eye coordination calculation reference can be made to U.S. Provisional Patent Application Ser. No. 62/801,734, filed Feb. 6, 2019. The entire contents of each of the above applications are hereby incorporated by reference.

With continued reference to FIG. 2, the linkage 12 includes the first link 12a, a second link 12b, a third link 12c, and a fourth link or rail 12d. Each link is pivotally coupled to at least one other link about a single degree of freedom joint as detailed below. The second link 12b includes a first portion that is pivotally coupled to a second portion of the first link 12a by a second joint $J_2$ and a first portion of the third link 12c is pivotally coupled to a second portion of the second link by a third joint $J_3$. The second and third links 12b, 12c are pivotal about axes of the second and third joints $J_2$, $J_3$ that are parallel to one another and perpendicular to the axis of the first joint $J_1$. In embodiments, movement of the second and third links 12b, 12c about the second and third joints $J_2$, $J_3$ is linked such that movement of the second link 12b about the second joint $J_2$ is equal and opposite to movement of the third link 12c about the third joint $J_3$ such that the third link 12c remains parallel to the first link 12b. The fourth link 12d is coupled to a second portion of the third link 12c about a fourth joint $J_4$. Movement of the fourth link 12d about the fourth joint $J_4$ is about an axis parallel to the axes of the second and third joints $J_2$, $J_3$.

The linkage 12 includes an instrument drive unit (IDU) 200 that is slidably supported along the fourth link 12d to define a linear fifth joint $J_5$ which allows the IDU 200 to move along a tool axis T-T that is parallel to a longitudinal axis of the fourth link 12d. A sixth joint $J_6$ is a roll joint of the IDU 200 about the tool axis T-T which permits the IDU 200, and thus the tool 20, to rotate about the tool axis T-T.

With reference to FIGS. 3-6, the IDU 200 includes a housing 210 having motors 220, 230, 240, 250; torque transducers 222, 232, 242, 252; a mounting plate 260; a control board 270; and a rear plate 280. Each motor 220, 230, 240, 250 is mounted to the mounting plate 260 by a respective one of the torque transducers 222, 232, 242, 252. The motors 220, 230, 240, 250 are arranged about a central longitudinal axis of the IDU 200 which is coaxial with the tool axis T-T. Each torque transducer 222, 232, 242, 252 includes a torque sensor, e.g., torque sensor 224, 234, that is configured to measure an applied torque of the respective motor in real time. The applied torque of the motors 220, 230, 240, 250 may be used to in a control algorithm to operate the tool 20 (FIG. 2). For a detailed discussion of exemplary control algorithms, reference can be made to U.S. Provisional Patent Application Ser. No. 62/776,285, filed Dec. 6, 2018, the entire contents of which are hereby incorporated by reference.

Figure 7:
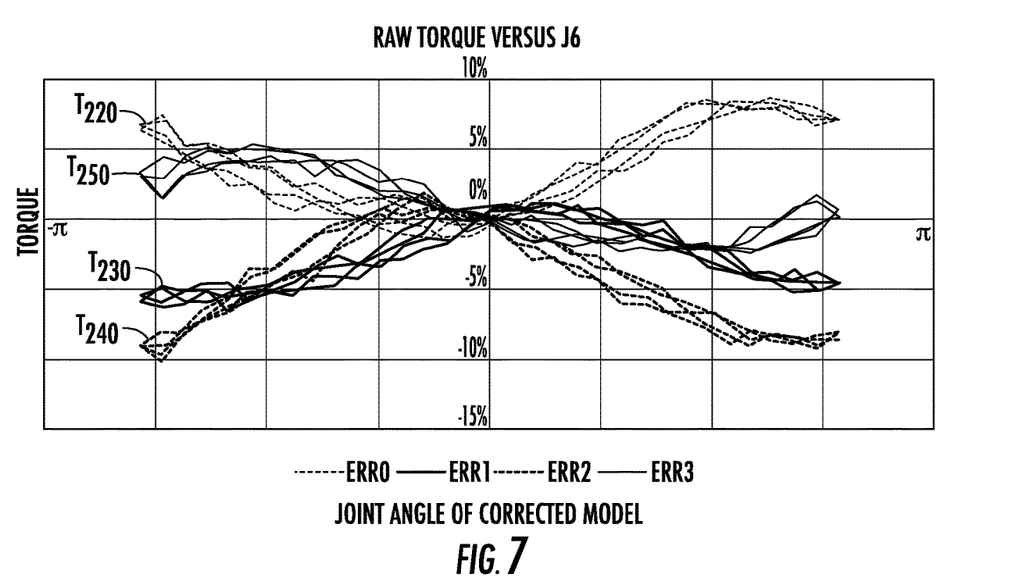
FIG. 7 is a graph illustrating a percent error in a torque reading of each motor of the IDU of FIG. 3 during a complete rotation of the IDU about joint 6 as shown in FIG. 2.

As noted above, the linkage 12 (FIG. 2) moves such that the pose of the linkage 12 changes forces on the tool 20 vary. In particular, gravity or gravitational forces on the tool 20 vary as the pose of the linkage 12 changes. In addition, the motors 220, 230, 240, 250 are mounted to the mounting plate 260 in a cantilevered manner by the torque transducers 222, 232, 242, 252 such that the gravity forces on the motors 220, 230, 240, 250 may affect the applied torque measured by the torque sensors, e.g., torque sensors 224, 234. For example, FIG. 7 shows the torque T of each motor, e.g., any one of motors 220, 230, 240, 250, as the IDU 200 is rotated about the tool axis T-T, e.g., joint $J_6$, with the remainder of the joints of the linkage 12 fixed. In particular, it is clear that the torque T of each motor 220, 230, 240, 250 varies along a curved path as the IDU 200 is rotated about the tool axis T-T. This variation can be attributed to the changes in the force of gravity acting on the motors 220, 230, 240, 250 and/or the tool 20 as the IDU 200 is rotated. Variations are seen when the linkage 12 is moved about other joints, e.g., joints $J_1$-$J_5$ of the linkage. However, depending on the particular joint, the torque T of the motors 220, 230, 240, 250 may vary in concert with one another and may vary by similar amounts or different amounts.

To determine the forces on the motors 220, 230, 240, 250, the pose of the IDU 200 being supported by the linkage 12 within the world frame $F_w$ may be calculated from the position of each of the joints $J_1$-$J_6$ and the position of $J_1$ within the world frame $F_w$. However, this calculation may require significant processing and would estimate the pose of the linkage 12 through a series of measurements, with a tolerance of each measurement inducing potential error in the final calculation of the pose of the IDU 200 and the resulting torque T of each motor 220, 230, 240, 250 as a result of gravitational forces.

Figure 3:
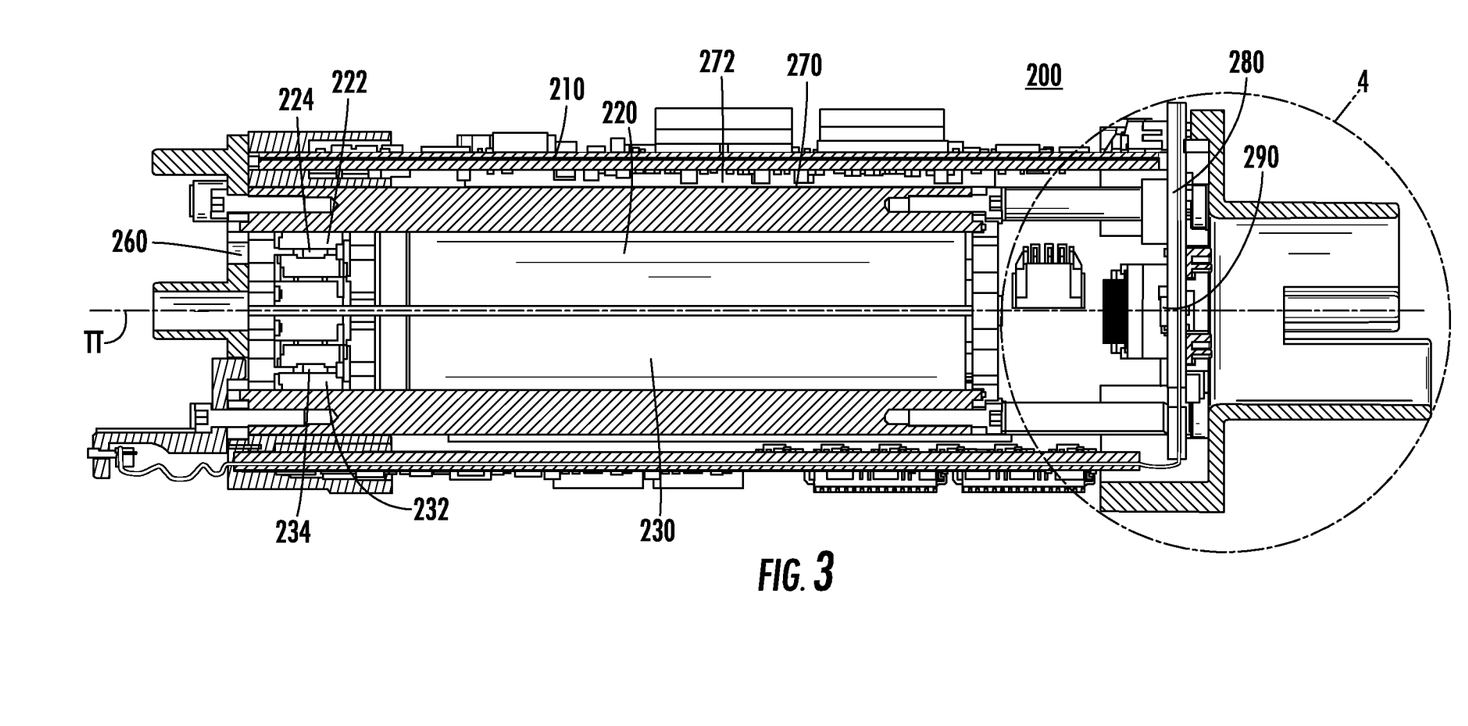
FIG. 3 is a cutaway view showing internal components of an IDU of the robot base of FIG. 2.
Figure 4:
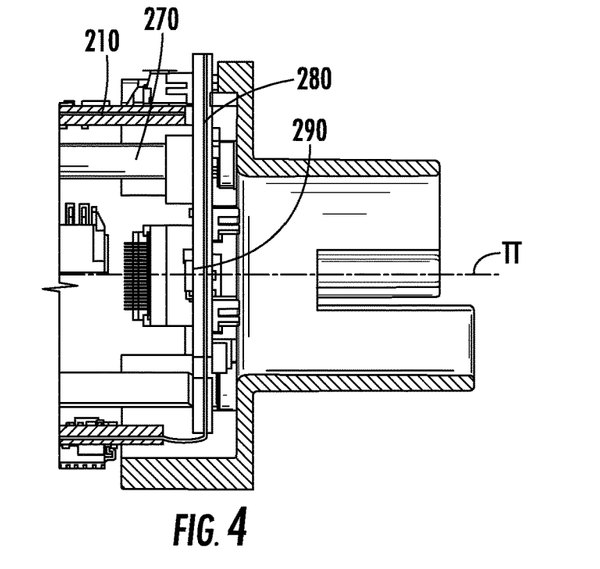
FIG. 4 is an enlarged view of the indicated area of detail of FIG. 3.
Figure 5:
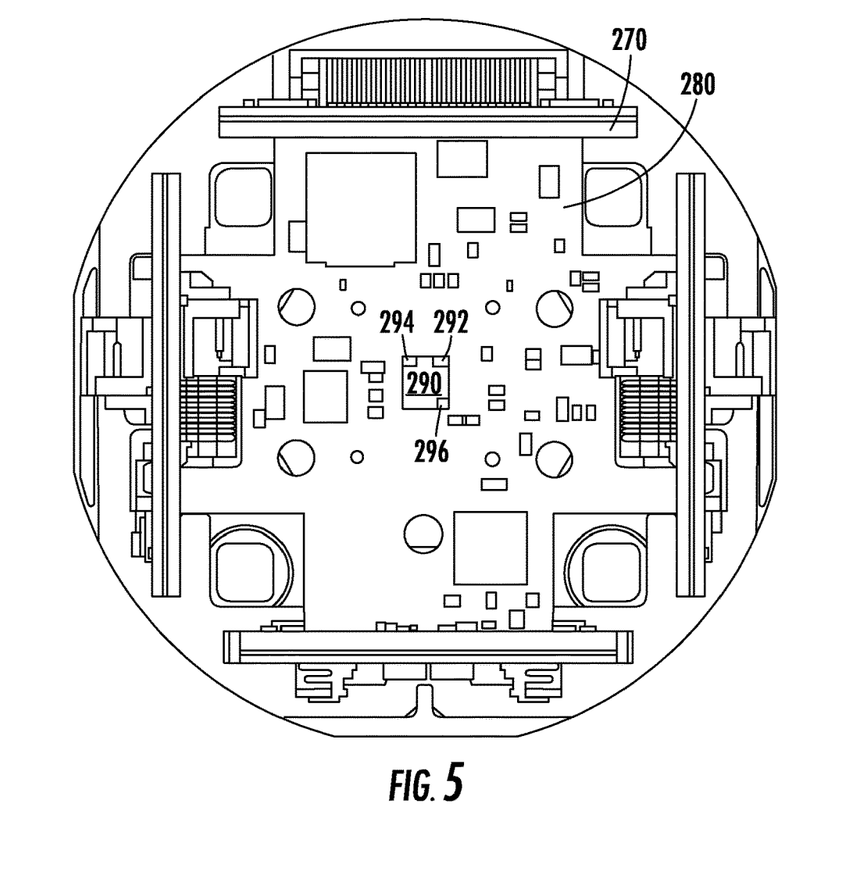
FIG. 5 is a plan view of a rear plate of the IDU of FIG. 3.
Figure 6:
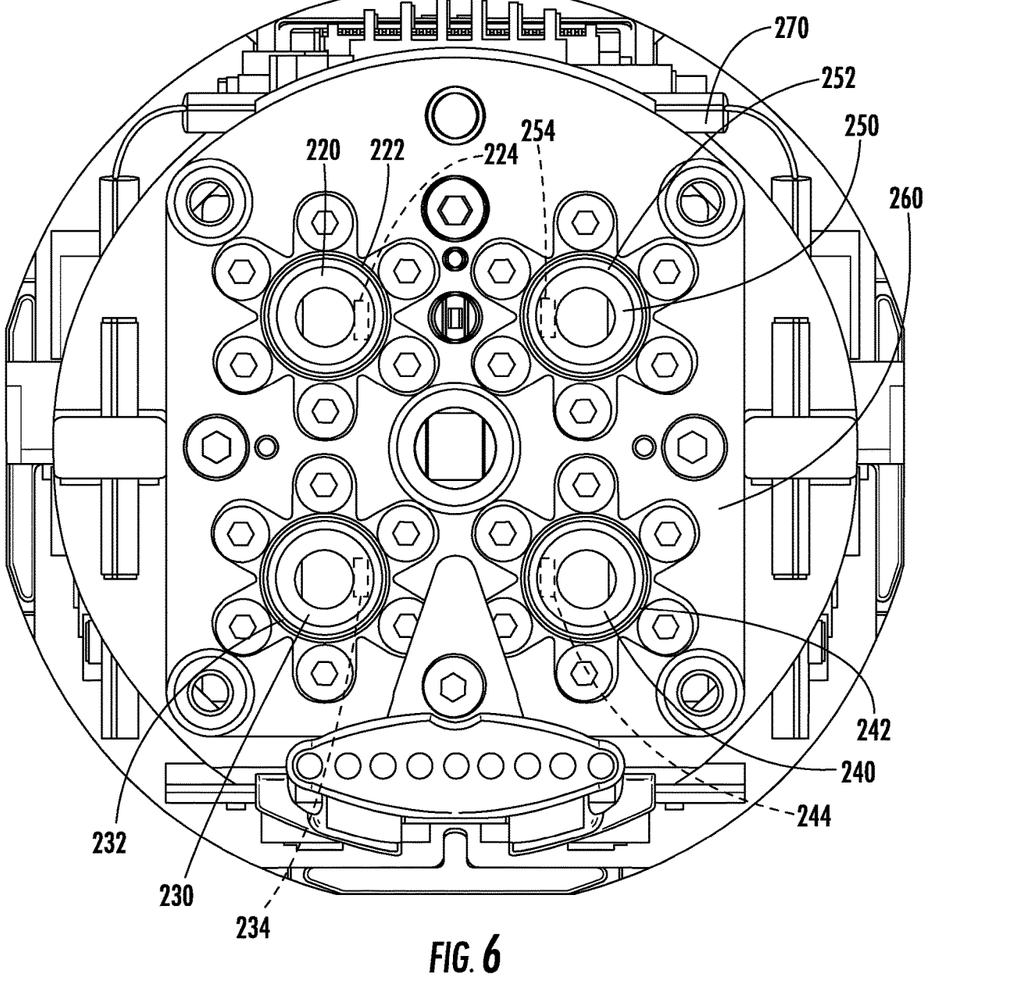
FIG. 6 is a front cutaway view of the IDU of FIG. 3.

To more accurately determine the pose of the IDU 200 and the torque T of each motor 220, 230, 240, 250, the IDU includes an inertial measurement unit (IMU) 290 secured to the rear plate 280 of the IDU 200. The IMU 290 may be a standalone unit or may be disposed a circuit board 282 that is secured to the rear plate 280. The IMU 290 is in communication with the control board 270. For example, the IMU 290 may be attached to or disposed on the circuit board 282 that is connected to the control board 260 via a connector 284. In embodiments, the IMU 290 is in wireless communication with the control board 270. The control board 270 may include a controller 272.

The IMU 290 includes an accelerometer 292 and a gyroscope 294 to determine orientation of the IDU 200. In embodiments, the IMU 290 also includes a compass 296 to assist in determining an orientation of the IDU 200. The IMU 290 is positioned such that the tool axis T-T passes through the IMU 290. Placing the IMU 290 along the tool axis T-T which is the axis of rotation of the IDU 200 may simplify the calculation for gravity compensation.

Figure 8:
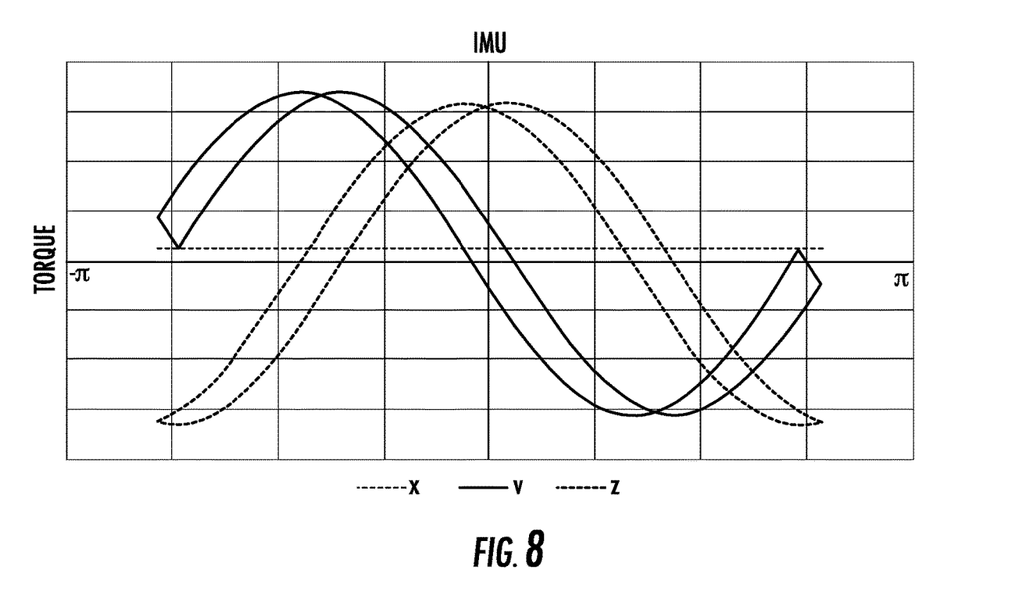
FIG. 8 is a graph illustrating readings of an IMU of the IDU of FIG. 3 during a complete rotation of the IDU about joint 6 as shown in FIG. 2.
Figure 9:
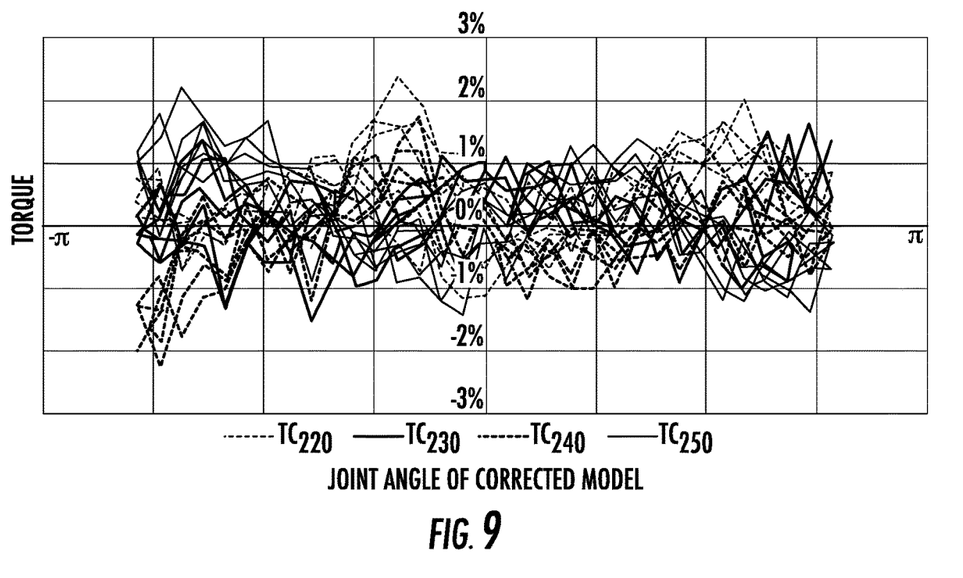
FIG. 9 is a graph illustrating a percentage error in a corrected torque reading of each motor of the IDU of FIG. 3 during a complete rotation of the IDU about joint 6 as shown in FIG. 2.

To calibrate the IMU 290, the tool 20 (e.g., a calibration fixture) is configured to determine calibration readings of the IMU 290 and convert these calibration readings into readings of the torque sensors 224, 234, 244, 254 for a plurality of poses of the linkage 12. For example, as shown in FIG. 8 the IMU 290 provides x, y, and z correction values as the joint angle of $J_6$ is varied in each direction. These x, y, and z correction values can be applied to torque measured by each of the torque sensors 224, 234, 244, 254 based on the pose of the IDU 200. Continuing the previous example and as shown in FIG. 9, when the correction values are applied to the torque measured by each of the torque sensors 224, 234, 244, 254, an error of the corrected torque values is significantly reduced across the range of motion about joint $J_6$. Specifically, the error is in a range of about −2% to about 2% for the corrected torque values when compared to a range of about −10% to about 9% for the raw or measured torque values. Increased accuracy in the corrected torque values may allow for a lower pretension for one or more of the motors 220, 230, 240, 250. Reducing the pretension of one or more of the motors 220, 230, 240, 250 may improve instrument life and/or reduce the cost of a surgical procedure using the robotic surgical system 1 (FIG. 1).

A map may be created to determine correction values for a plurality of poses of the linkage 12 by manipulating the pose of the linkage 12 with a calibration fixture, e.g., tool 20. The map may include correction values for every pose of the IDU in six degrees of freedom. This map may be used to create functions for the readings of the IMU 290 or can be a table used as a look up during a surgical procedure to provide correction values based on the pose of the linkage 12. The map may be created during a manufacture of the surgical robot 10 or may be created by a calibration program prior to a surgical procedure.

Figure 10:
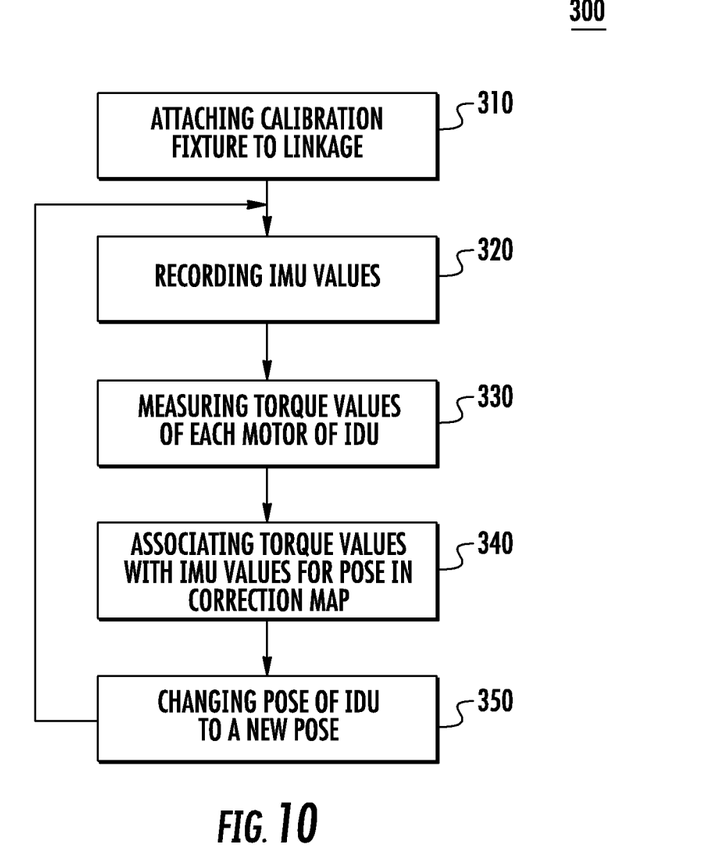
FIG. 10 is a flow chart illustrating an exemplary method of generating a calibration map to calibrate an IMU.

Referring to FIG. 10, a method 300 for generating a calibration map is provided in accordance with the present disclosure with reference to the robotic surgical system of FIGS. 1-6. Initially, a calibration fixture is attached to an end of linkage 12 as a tool 20 (Step 310). The calibration fixture is configured to detect torque of each of the motors 220, 230, 240, 250. With the calibration fixture attached, readings of values from the IMU 290 are recorded (Step 320). The torque values of each motor 220, 230, 240, 250 are also recorded (Step 330). The torque values of each motor 220, 230, 240, 250 may be measured by a respective one of the torque sensors 224, 234, 244, 254 or may be measured by the calibration fixture. The values of the IMU 290 and the torque values of each motor 220, 230, 240, 250 are associated with one another in a calibration map (Step 340). The calibration map may be a matrix that is stored in a memory. With the values of the IMU 290 and torque values associated with one another in the calibration map, the IDU 200 is moved to a new pose (Step 350) and the steps 320-340 are repeated for the new pose. This process is recorded until each pose of the IDU 200 is included in the calibration map or enough points are recorded in the calibration map to generate one or more equations to determine correction values for each motor 220, 230, 240, 250 for poses of the IDU 200.

Figure 11:
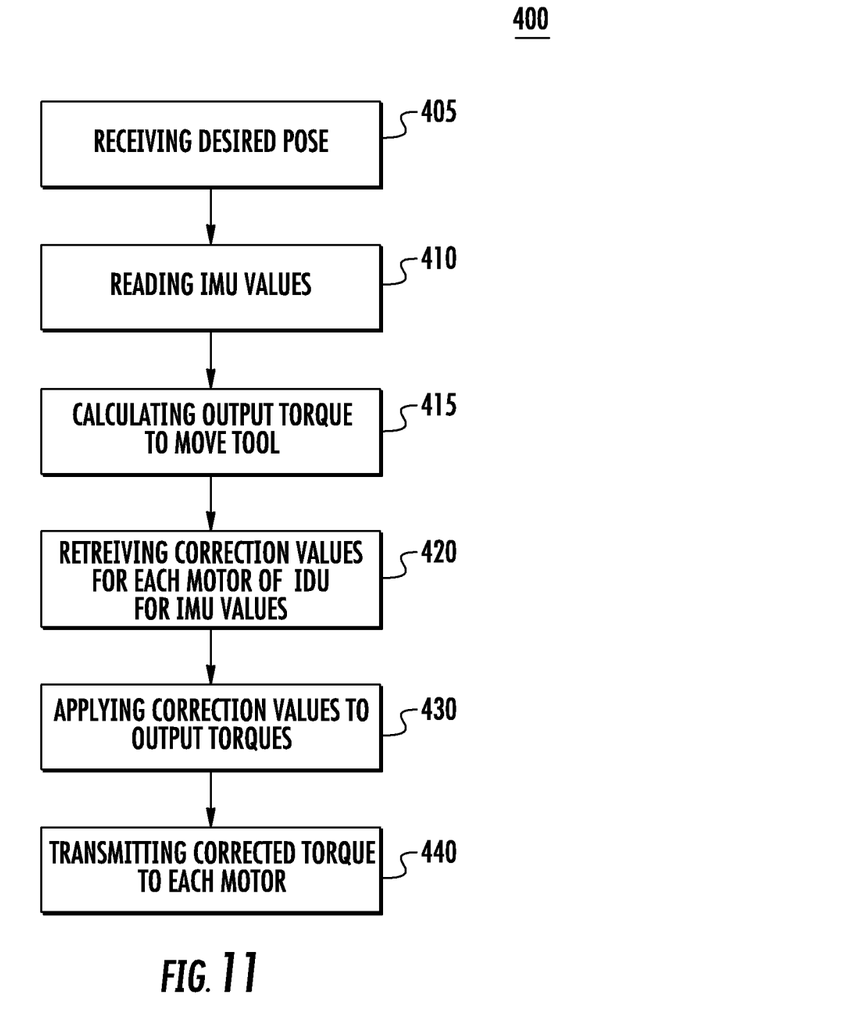
FIG. 11 is a flow chart illustrating an exemplary method of controlling a tool.

With reference to FIG. 11, a method 400 of controlling an IDU is described in accordance with the present disclosure with reference to the robotic surgical system 1 and the IDU 200 of FIGS. 1-6. The controller 272 of the IDU 200 receives a desired pose of the tool 20 (Step 405). The desired pose may be received from the processing unit 30, controller 32, 34, or the ADU 35. To determine the current pose of the IDU 200, the controller 272 reads values of the IMU 290 (Step 410). The values of the IMU 290 are unique for each pose of the IDU 200 and are stored in the calibration map as detailed above. With the pose of the IDU 200 determined from the values of the IMU 290, the controller 272 calculates an output torque for each motor 220, 230, 240, 250 to manipulate the pose of the tool 20 to the desired pose (Step 415). The controller 272 also retrieves or determines correction values for each motor 220, 230, 240, 250 from the pose of the IDU 200 determined in Step 410 (Step 420). The controller 272 applies the correction values to the output torque for each motor 220, 230, 240, 250 calculated in step 415 to generate a corrected torque for each motor 220, 230, 240, 250 (Step 430). The controller 272 transmits a corrected torque to each motor 220, 230, 240, 250 such that the IDU 200 manipulates the tool 20 to the desired pose (Step 440).

Figure 12:
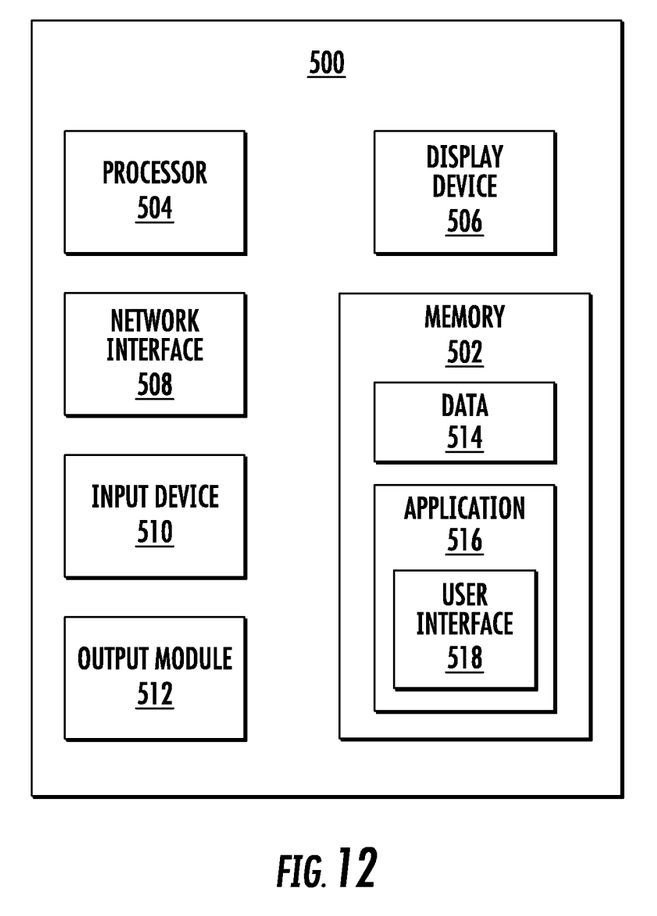
FIG. 12 is a schematic block diagram of an illustrative embodiment of a controller that may be employed in various embodiment of the present system, for instance, as part of the robotic surgical system of FIG. 1.

With reference to FIG. 12, a computing device may be employed in accordance with various embodiments herein. For example, the input shaper algorithms detailed above may be stored in and executed in a computing device. Although not explicitly shown, in some embodiments, the computing device 300, or one or more of the components thereof, may further represent one or more components (e.g., the processing unit 30, the base 18, the controllers 32, 34, the ADU 35, the controller 272, and/or the like) of the robotic surgical system 1. The computing device 300 may, in various embodiments, include one or more memories 502, processors 504, display devices 506, network interfaces 508, input devices 510, and/or output modules 512. The memory 502 includes non-transitory computer-readable storage media for storing data and/or software that is executable by the processor 504 and which controls the operation of the computing device 300. In embodiments, the memory 502 may include one or more solid-state storage devices such as flash memory chips. Alternatively, or in addition to the one or more solid-state storage devices, the memory 502 may include one or more mass storage devices connected to the processor 504 through a mass storage controller (not shown in FIG. 12) and a communications bus (not shown in FIG. 12). Although the description of computer readable media contained herein refers to a solid-state storage, it should be appreciated by those skilled in the art that computer-readable storage media can be any available media that can be accessed by the processor 504. That is, computer readable storage media includes non-transitory, volatile and non-volatile, removable and non-removable media implemented in any method or technology for storage of information such as computer-readable instructions, data structures, program modules or other data. Examples of computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 300.

In some embodiments, the memory 502 stores data 514 and/or an application 516. In some aspects the application 516 includes a user interface component 518 that, when executed by the processor 504, causes the display device 506 to present a user interface (not shown in FIG. 12). The network interface 508, in some embodiments, is configured to couple the computing device 300 and/or individual components thereof to a network, such as a wired network, a wireless network, a local area network (LAN), a wide area network (WAN), a wireless mobile network, a Bluetooth network, the Internet, and/or another type of network. The input device 510 may be any device by means of which a user may interact with the computing device 300. Examples of the input device 510 include without limitation a mouse, a keyboard, a touch screen, a voice interface, and/or the like. The output module 512 may, in various embodiments, include any connectivity port or bus, such as, for example, a parallel port, a serial port, a universal serial bus (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An instrument drive unit configured to manipulate a tool, the instrument drive unit comprising:
    a housing defining a central longitudinal axis and configured to couple to the tool;
    at least one motor disposed in the housing and including a torque sensor configured to measure torque of the at least one motor;
    an inertial measurement unit disposed along the central longitudinal axis within the housing and configured to measure an orientation of the instrument drive unit; and
    a controller configured to:
        generate a calibration map between the orientation of the instrument drive unit and the torque of the at least one motor;
        calculate an output signal to control the at least one motor to manipulate the tool;
        determine a pose of the instrument drive unit based on the orientation of the instrument drive unit;
        retrieve a correction value from the calibration map based on the pose of the instrument drive unit; and
        generate a corrected output signal to manipulate the tool by adjusting the output signal based on the correction value, wherein the corrected output signal compensates for the pose of the instrument drive unit.

2. The instrument drive unit according to claim 1, wherein the inertial measurement unit includes a gyroscope and an accelerometer.

3. The instrument drive unit according to claim 2, wherein the inertial measurement unit includes a compass.

4. The instrument drive unit according to claim 1, wherein the inertial measurement unit is configured to measure the orientation of the instrument drive unit based on gravity acting on the inertial measurement unit.

5. The instrument drive unit according to claim 1, wherein the at least one motor is configured to receive the corrected output signal and to manipulate the tool in response to the corrected output signal.

6. The instrument drive unit according to claim 5, further comprising a mounting plate at a first end of the instrument drive unit, the at least one motor secured to the mounting plate by the torque sensor.

7. The instrument drive unit according to claim 6, further comprising a rear plate at a second opposite end of the instrument drive unit, the inertial measurement unit secured to the rear plate.

8. The instrument drive unit according to claim 7, further comprising a control board extending between the rear plate and the mounting plate, the controller disposed on the control board.

9. The instrument drive unit according to claim 1, further comprising:
    a first motor;
    a second motor;
    a third motor; and
    a fourth motor:
    wherein the first, second, third, and fourth motors are disposed within the housing and arranged about the central longitudinal axis, each of the second, third, and fourth motors configured to receive the corrected output signal and to manipulate the tool in response to the corrected output signal.

10. The instrument drive unit according to claim 9, further comprising:
    a second torque sensor disposed within the housing and configured to measure a torque of the second motor;
    a third torque sensor disposed within the housing and configured to measure a torque of the third motor; and
    a fourth torque sensor disposed within the housing and configured to measure a torque of the fourth motor.

11. A surgical robot comprising:
    a base;
    a linkage supported by the base;
    a tool; and
    an instrument drive unit supported by the linkage and configured to couple to and manipulate the tool, the instrument drive unit comprising:
        a housing defining a central longitudinal axis;
        at least one motor disposed in the housing and including a torque sensor configured to measure torque of the at least one motor;
        an inertial measurement unit disposed along the central longitudinal axis within the housing and configured to measure an orientation of the instrument drive unit; and
        a controller configured to:
            generate a calibration map between the orientation of the instrument drive unit and the torque of the at least one motor;
            calculate an output signal to control the at least one motor to manipulate the tool;

determine a pose of the instrument drive unit based on the orientation of the instrument drive unit;

retrieve a correction value from the calibration map based on the pose of the instrument drive unit; and generate a corrected output signal to manipulate the tool by adjusting the output signal based on the correction value, wherein the corrected output signal compensates for the pose of the instrument drive unit.

12. The surgical robot according to claim 11, wherein the tool is supported about a tool axis coaxial with the central longitudinal axis.

13. A method of controlling an instrument drive unit with a controller, the method comprising:

determining a pose of the instrument drive unit based on an orientation of the instrument drive unit measured by an inertial measurement unit disposed along a central longitudinal axis within a housing of the instrument drive unit, wherein the instrument drive unit is coupled to a tool and includes at least one motor configured to manipulate the tool, the at least one motor disposed in the housing and a torque sensor configured to measure torque of the at least one motor;

generating a calibration map between the orientation of the instrument drive unit and the torque of the at least one motor;

calculating an output torque to control the at least one motor to manipulate the tool;

retrieving a correction value from the calibration map based on the pose of the instrument drive unit;

calculating a corrected torque to manipulate the tool by adjusting the output torque based on the correction value; and transmitting the corrected torque to a motor of the instrument drive unit.

14. The method according to claim 13, further comprising receiving a desired pose of the tool and calculating the output torque to manipulate the tool from a current pose to the desired pose.

15. The method according to claim 13, wherein determining the pose of the instrument drive unit includes measuring gravity acting on the inertial measurement unit with a gyroscope and an accelerometer of the inertial measurement unit.

* * * * *